United States Patent
Turcott (10) Patent No.: US 6,945,939 B2
(45) Date of Patent: Sep. 20, 2005

(54) HEMODYNAMIC ANALYSIS (75) Inventor: Robert G. Turcott, Mountain View, CA (US)

(73) Assignee: Pacesetter, Inc., Sylmar, CA (US)

(*) Notice: Subject to any disclaimer, the term of this patent is extended or adjusted under 35 U.S.C. 154(b) by 335 days.

(21) Appl. No.: 10/273,604

(22) Filed: Oct. 18, 2002

(65) Prior Publication Data

US 2004/0077953 A1 Apr. 22, 2004

(51) Int. Cl.[7] .............................................. A61B 5/02
(52) U.S. Cl. ........................ 600/481; 600/300; 607/4; 607/5; 607/9
(58) Field of Search ................. 600/300, 301, 600/310, 322–340, 361, 365, 481, 485, 504–513, 516, 528, 529, 531; 607/2, 4–6, 9, 17–26, 119

(56) References Cited

U.S. PATENT DOCUMENTS

| | | | |
|---|---|---|---|
| 4,303,075 A | 12/1981 | Heilman et al. | 128/419 |
| 4,360,029 A * | 11/1982 | Ramsey, III | 600/494 |
| 4,457,315 A * | 7/1984 | Bennish | 600/517 |
| 5,024,222 A | 6/1991 | Thacker | 128/419 |
| 5,129,394 A | 7/1992 | Mehra | 128/419 PG |
| 5,168,869 A | 12/1992 | Chirife | 128/419 |
| 5,392,781 A * | 2/1995 | Phillipps et al. | 600/493 |
| 5,487,752 A | 1/1996 | Salo et al. | 607/17 |
| 5,527,347 A * | 6/1996 | Shelton et al. | 607/9 |
| 5,540,727 A | 7/1996 | Tockman et al. | 607/18 |
| 5,549,655 A | 8/1996 | Erickson | 607/42 |
| 5,551,438 A * | 9/1996 | Moses | 600/485 |
| 5,554,177 A | 9/1996 | Kieval et al. | 607/17 |
| 5,626,620 A | 5/1997 | Kieval et al. | 607/9 |
| 5,626,623 A | 5/1997 | Kieval et al. | 607/23 |
| 5,700,283 A | 12/1997 | Salo | 607/17 |
| 5,772,601 A * | 6/1998 | Oka et al. | 600/495 |
| 5,792,195 A * | 8/1998 | Carlson et al. | 607/17 |
| 5,800,471 A | 9/1998 | Baumann | 607/25 |
| 5,836,987 A | 11/1998 | Baumann et al. | 607/17 |
| 5,941,829 A * | 8/1999 | Saltzstein et al. | 600/509 |
| 5,981,176 A | 11/1999 | Wallace | 607/18 |
| 6,044,298 A | 3/2000 | Salo et al. | 607/17 |
| 6,058,329 A | 5/2000 | Salo et al. | 607/17 |
| 6,076,005 A | 6/2000 | Sontag et al. | 600/413 |
| 2002/0115939 A1 | 8/2002 | Mulligan et al. | 600/510 |

FOREIGN PATENT DOCUMENTS

| | | | |
|---|---|---|---|
| EP | 0347708 A1 | 6/1989 | A61B/5/02 |
| WO | WO 01/56651 A1 | 8/2001 | A61N/1/365 |
| WO | WO 01/80947 A1 | 11/2001 | A61N/1/368 |

* cited by examiner

Primary Examiner—Robert L. Nasser
Assistant Examiner—Patricia C. Mallari (57) ABSTRACT To track significant changes in a hemodynamic variable of a living body regardless of measurement noise induced by cyclical functions of the body, the hemodynamic variable is measured at substantially the same instant during several cycles and the measured values compared to identify any statistically significant changes. The measurements may be discrete or continuous. The heart may be stimulated by a cardiac device during some of the cycles and parameters of the device such as the A-V delay of a pacemaker may be adjusted in accordance with the measured change in the hemodynamic variable, which may be, among others, blood pressure or blood volume.

39 Claims, 8 Drawing Sheets

FIG. 2a Analysis A: Unpaired

FIG. 2b Analysis B: Paired; Respiration Asynchronous

FIG. 2c Analysis C: Paired; Respiration Synchronous

HEMODYNAMIC ANALYSIS

FIELD OF THE INVENTION

The field of the present invention relates to monitoring hemodynamic parameters in a living body, and more particularly to techniques for accurately detecting changes in hemodynamic parameters and measuring such parameters.

BACKGROUND OF THE INVENTION

Hemodynamic parameters are measurable attributes associated with the circulatory system of a living body, such as, for example, blood flow rate, blood pressure, volume of the vasculature, volume of the cardiac chambers, stroke volume, oxygen consumption, heart sounds, respiration rate, tidal volume, blood gases, pH, and acceleration of the myocardium. There are numerous medical reasons for sensing and tracking changes in hemodynamic parameters, including the proper operation of implantable cardiac stimulation devices.

Implantable cardiac stimulation devices (such as pacemakers, defibrillators, and cardioverters) are designed to monitor and stimulate the heart of a patient who suffers from a cardiac arrhythmia. Using leads connected to the patient's heart, these devices typically stimulate the cardiac muscles by delivering electrical pulses in response to detected cardiac events which are indicative of a cardiac arrhythmia. Properly administered therapeutic electrical pulses often successfully reestablish or maintain the heart's regular rhythm.

Modern implantable devices have a great number of adjustable parameters that can be tailored to a particular patient's therapeutic needs. Any of a number of parameters that define pacing characteristics may be optimized. Adjustable parameters may include, for example, the atrioventricular (A-V) delay, the R-R interval, and the pacing mode (e.g. pace and sense in the ventricle, inhibited (VVI), pace and sense in the atrium and the ventricle, both triggered and inhibited (DDD), etc.). As an example, the A-V delay is typically optimized in dual-chamber (atrial and ventricular) pacemakers to time the ventricular contraction such that the contribution of the atrial contraction is maximally exploited. As another example, ventricular synchronization may be optimized in biventricular pacing for heart failure by adjusting the timing at which pacing pulses are delivered to various cardiac sites.

Typically, interchamber pacing intervals (such as A-V delay in dual chamber pacemakers and RV-LV delay in biventricular pacemakers) are set to default nominal values, or else relatively labor-intensive methods are used to measure hemodynamic variables in an effort to optimize some or all of the parameters at the time a cardiac stimulation device is implanted. Examples of measurements that may be carried out in connection with device programming include ultrasound to measure mitral flow and/or ejection fraction and left heart catheterization to measure the rate of change of left ventricular pressure during systole, which is a measure of contractility and mechanical efficiency.

One common technique for setting device parameters involves manually varying the operating parameters of a pacing system while monitoring one or more physiological variables. Typically, the optimum value for a parameter is assumed to be that which produces the maximum or minimum value for the particular physiological variable. This manual method can be time-consuming, during which the underlying physiologic substrate may change and give rise to inaccurate assessment of cardiac performance. Additionally, the manual method is prone to errors occurring during data gathering and transcription.

An automated technique for setting at least one type of device parameter entails systematically scanning through a series of available A-V pulse delays at a fixed heart rate while monitoring a measure of cardiac output, then setting the A-V pulse delay to the value which resulted in the maximum cardiac output. Another technique selects the A-V pulse delay by maximizing the measured value (e.g. by electrical impedance) of a parameter such as stroke volume.

Another method for automatically selecting a cardiac performance parameter entails periodically pacing the heart for a short period of time with stimulating pulses having a modified pacing parameter value, then allowing the heart to return to a baseline value for a relatively long time. The cardiac performance parameter is monitored both during and after the heart is paced to determine if it has improved, degraded, or remained the same. The heart is then paced with a modified pacing parameter value and the process is repeated.

The optimization of pacing parameters is not necessarily critical in patients with relatively normal myocardium, although it may be beneficial to them. These patients have the necessary cardiac reserve to compensate for programming errors. It is patients with depressed cardiac function that are much more sensitive to factors such as pacing rate and A-V delay. Current optimization techniques are time-consuming and labor intensive. Furthermore, they are prone to error because they do not account for variability in the measured hemodynamic signals that often obscures real and significant changes in hemodynamic status and complicates measuring the absolute values of hemodynamic parameters. What is now needed is a method or system for detecting changes in hemodynamic parameters as well as obtaining accurate absolute measurements of such parameters.

SUMMARY

In a first aspect, a method is provided for monitoring changes in a living body, comprising measuring a hemodynamic variable of a living body during two different cycles of a cyclical function of the body, the hemodynamic variable being measured at substantially the same instant in each cycle, and comparing values of the hemodynamic variable measured during the two different cycles.

In another aspect, a method is provided for operating a cardiac stimulation device implanted in a living body, comprising measuring a hemodynamic variable of the body at a first instant during a first cycle of a selected cyclical function of the body, operating the cardiac device to stimulate the heart of the body during a second cycle of the function, measuring the hemodynamic variable at an instant during the second cycle that is substantially the same as the first instant, and adjusting an operating parameter of the cardiac device in accordance with a difference between values of the hemodynamic variable measured during the first and second cycles.

In further aspects, the cyclical function may be, for example, respiration, heart beat, circadian rhythm, digestion, or locomotion. Further, the hemodynamic variable may be, for example, blood flow rate, blood pressure, volume of vasculature, volume of cardiac chambers, stroke volume, oxygen consumption, heart sounds, respiration rate, tidal volume, blood gases, pH, or acceleration of the myocardium.

In a still further aspect, the foregoing method may further comprise measuring the hemodynamic variable at a second instant during a third cycle of the cyclical function, operating the cardiac device to stimulate the heart during a fourth cycle of the function, measuring the hemodynamic variable at an instant during the fourth cycle that is substantially the same as the second instant, and adjusting the operating parameter a second time in accordance with a difference between values of the hemodynamic variable measured during the third and fourth cycles.

In another aspect, an apparatus for monitoring changes in a living body comprises a detector configured for measuring a hemodynamic variable of a living body during two different cycles of a cyclical function of the body at substantially the same instant in each cycle; and a controller configured for comparing values of the hemodynamic variable measured during the two different cycles. The apparatus may be configured to be implanted in the living body.

Additional or alternative features, variations, enhancements, and advantages of the invention will also become further apparent from the detailed description and accompanying figures that follow.

DETAILED DESCRIPTION

In accordance with one embodiment as described herein, a method is provided for monitoring one or more hemodynamic parameters of a living body (e.g. a patient) to detect selectively significant changes in the parameters and to more accurately determine their absolute values. It is known that hemodynamic parameters can be affected by body functions, and more particularly by body functions that are cyclic in nature. For example, respiration is known to induce significant variability in hemodynamic measurements depending on the stage of the respiration cycle at which a particular hemodynamic parameter is measured. An improved technique for monitoring a hemodynamic parameter is hereby provided, wherein measurements of the parameter are taken at the same instant during each of a plurality of cycles of a body function. The measurements are then compared to detect any physiologically significant changes in the parameter. By comparing measurements taken at the same instant during each cycle of the function of interest (i.e. the function that impacts the parameter), the variability induced by the function into the hemodynamic parameter measurements can be effectively reduced or eliminated, and more accurate measurements of actual fluctuations of the hemodynamic parameters can thereby be taken without the distorting effect of the cyclic function.

The measurements may be taken at the same exact instant within each cycle or at substantially the same instant, that is, at an instant within the next cycle that is sufficiently near the instant at which the measurement was taken in the previous cycle to enable the techniques described herein to provide acceptable results, which may be a statistically acceptable correlation between the hemodynamic variable and the cyclic function. The range by which the instant at which the measurements are taken may be allowed to vary from cycle to cycle may depend, among others, on the cyclical function being tracked, the hemodynamic variable being measured, and the state of the patient (e.g. healthy or sick, exercising or at rest, asleep or awake), and in one embodiment may be determined empirically.

Hemodynamic parameters that may be measured more accurately by the techniques disclosed herein may include, by way of example only, blood flow rate, blood pressure, volume of vasculature, volume of cardiac chambers, stroke volume, oxygen consumption, heart sounds, respiration rate, tidal volume, blood gases, pH, and acceleration of the myocardium. These and other parameters may be affected by any one or more body functions including, for example, respiration, heart beat, circadian rhythm, digestion, and locomotion (e.g. walking, running, swimming). Some functions operate in cycles that are longer than other functions, such as digestion (which can take hours) versus the heart beat (which occurs approximately once every second). Each function generally impacts or affects each hemodynamic parameter to a different extent, that can vary from negligible to significant. As disclosed herein, these effects can be eliminated or reduced by conditioning the analysis of a hemodynamic parameter on the principal period (or periods) of variability.

In accordance with one embodiment as disclosed herein, changes in hemodynamic measurements taken in two different environmental settings are assessed by comparing measurements taken at the same instant during different cycles of the principal body function(s) (or period(s) of variability). As one example, arterial pressure may be measured during periods when the heart is paced (e.g. by a cardiac stimulation device such as a pacemaker) and during periods when it is not paced, so as to assess the effect of pacing with various parameters. One possible application may be to optimize the A-V delay of the pacemaker by incrementally adjusting the delay and thereafter pacing the heart with the new delay setting, and comparing the measured arterial pressure with the pressure measured during the non-paced cycle and/or the previous paced cycle (with a different A-V delay setting). The A-V delay could thereby be continuously adjusted to maintain a desired arterial pressure.

Alternatively, blood volume may be the hemodynamic variable that is measured and the A-V could be continuously adjusted so as to maximize the volume of blood pumped by the heart with each beat. By comparing the previously measured value for the hemodynamic variable (e.g. blood volume) with the latest measured value, the parameter (e.g. A-V delay) may be incrementally adjusted up or down to thereby adjust the value of the hemodynamic variable up or down, as may be desired. Other hemodynamic variables or other cardiac device parameters may require adjusting the parameter so as to minimize, rather than maximize, the hemodynamic variable, or to maintain the hemodynamic variable near an ideal, predetermined value.

Advantages of certain techniques as disclosed herein may be explained with reference to FIGS. 1a–1c and 2a–2c, wherein use of one method as disclosed herein is contrasted with two conventional alternative techniques for measuring changes in arterial pressure when atrial-synchronous pacing is delivered to the heart. One conventional approach is illustrated by Analysis A in FIG. 1a, wherein the average pressure during paced heart beats is compared to the average pressure during intrinsic, non-paced heart beats. The pressure is measured over substantial portion 10 of respiratory cycle 18 while the heart is not paced and then averaged, then once again measured and averaged over substantial portion 20 of respiratory cycle 28 while the heart is paced. As shown in FIG. 2a, the two average values are then compared statistically. In the example shown, it may be seen that the average values are different (80.9 non-paced and 79.9 paced) but the difference is small when compared to their standard deviation values (2.1 and 2.0 respectively). Statistical analysis of these values produces a p value of 0.43, thereby indicating that the difference between the two average values is highly non-significant. Thus, use of this technique would lead to the false conclusion that there is no difference in arterial pressure between paced and non-paced heart beats.

Figure 1A:
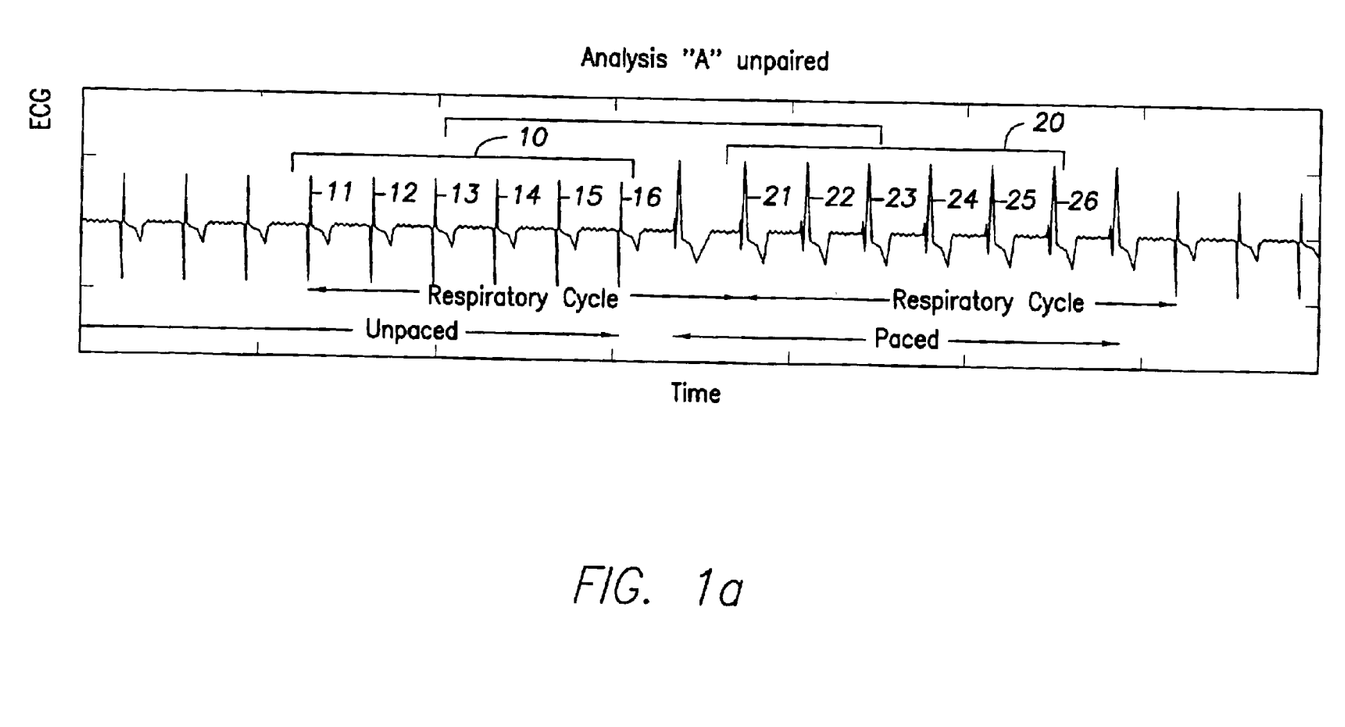
FIGS. 1a–1c depict a series of graphs evincing paced and non-paced heart beats (1a–1b) of a patient and the corresponding blood pressure (1c)
Figure 1B:
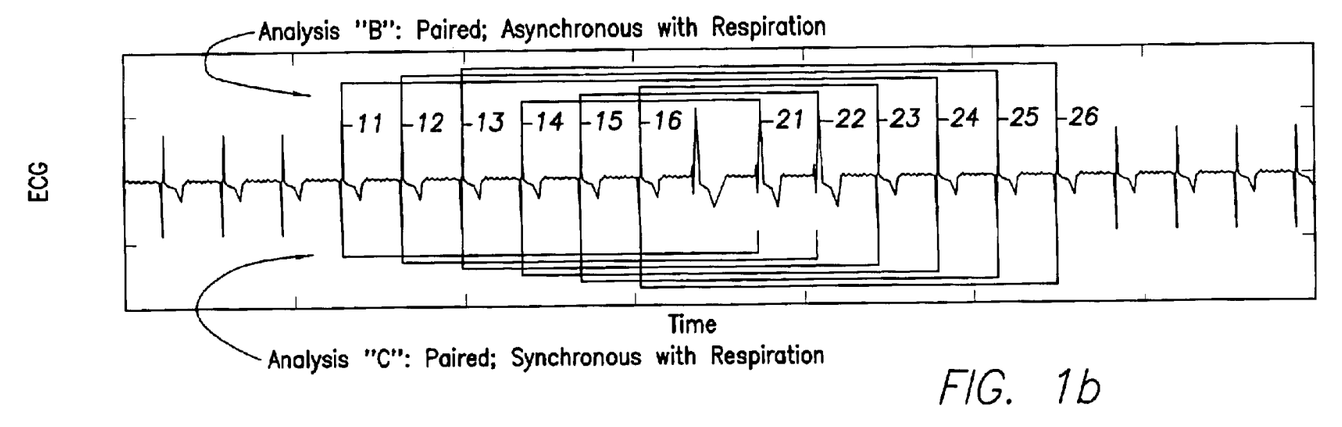
Figure 1C:
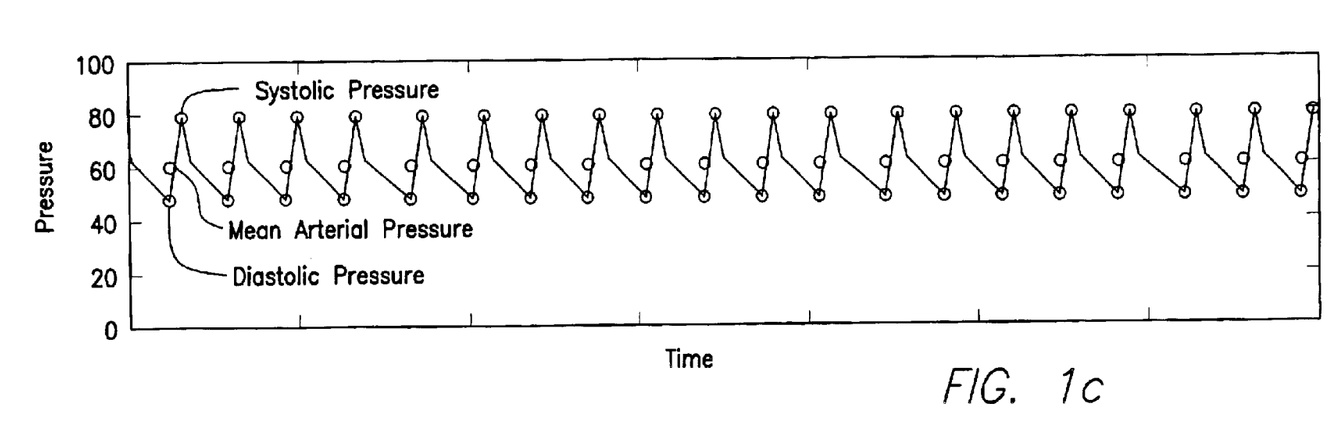
Figure 2A:
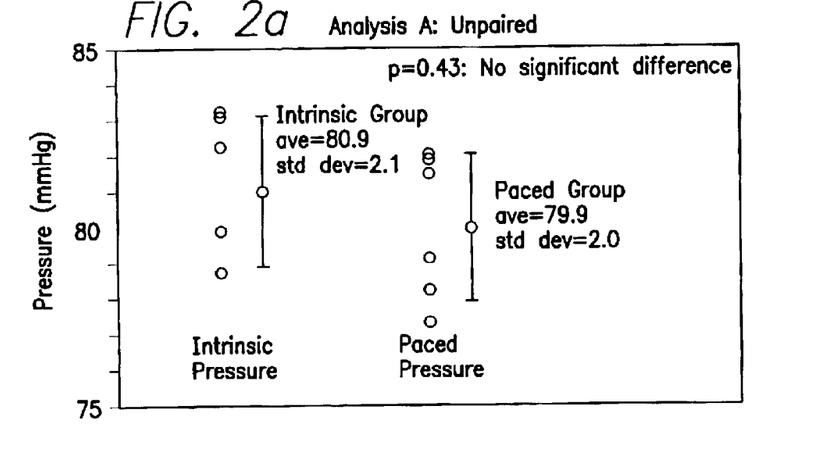
FIGS. 2a–2c are graphs reflecting statistical representation of the blood pressure data depicted in FIG. 1.
Figure 2B:
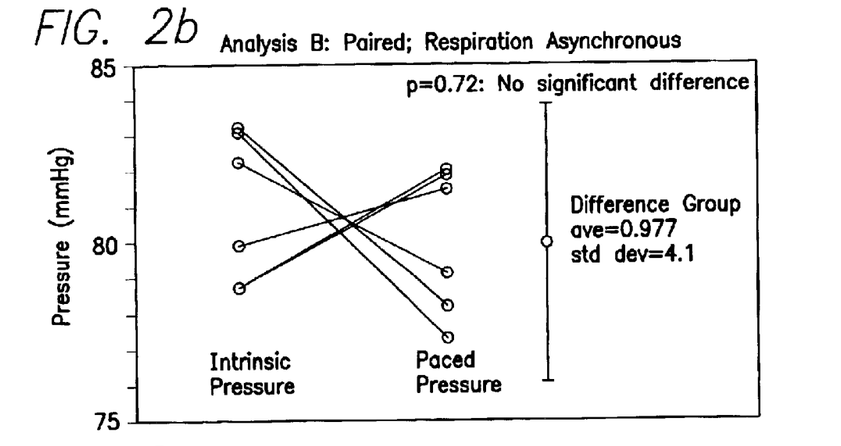

With reference now to FIG. 1b, an analysis is illustrated for performing a pair-wise comparison of data points without regard for the respiratory phase. As shown in Analysis B, paced heart beats are randomly paired with non-paced heart beats, e.g. non-paced beat 11 is paired with paced beat 24, 12 with 25, etc. The difference between each pair of beats is subsequently calculated and the average value and standard deviation value of these differences are next derived. Referring now to FIG. 2, it is shown that the average value of the differences (−0.977) is much smaller than the standard deviation value of 4.1. Thus, the use of this approach yields a p value of 0.72, again failing to indicate a significant difference in arterial pressure between paced and non-paced heart beats.

With continued reference to FIG. 1b, use of a method in accordance with one embodiment as disclosed herein is illustrated in Analysis C, wherein paced heart beats are paired with corresponding non-paced heart beats measured at the same instant in time (i.e. phase) during the paced and non-paced respiratory cycles 18, 28. Thus, non-paced heart beat 11 is paired with paced heart beat 21, 12 with 22, etc. As seen in FIG. 1b, both beats 11 and 21 occur in the beginning of the respective respiratory cycle, beats 12 and 21 are the next heart beats to occur after beats 11 and 21, etc. As before, the differences between the paired beats are calculated and the average value of the differences and their standard deviation is subsequently derived. As expected, and shown in FIG. 2c, the average value is still −0.977, but the standard deviation is now 0.347, thus indicating with extreme confidence (at a p value of 0.001) that the decrease in the arterial pressure measured during the paced respiratory cycle is statistically significant and thus associated with pacing the heart.

The analysis techniques described above and with respect to FIGS. 1 and 2 were shown for illustration purposes to be performed on pressure measurements during paced and non-paced heart beats. It must be understood that the method of the invention is not limited to this particular measurement paradigm, but rather may be utilized with other hemodynamic variables including, but not limited to, cardiac output, flow, stroke volume, and vascular volume. Furthermore, the method of the invention may be utilized with non-hemodynamic variables such as temperature. Additionally, the comparison analysis is not limited to paced vs. non-paced heart beats but may also be applied to other changes, such as changes in the A-V delay or in the RV-LV delay.

Figure 2C:
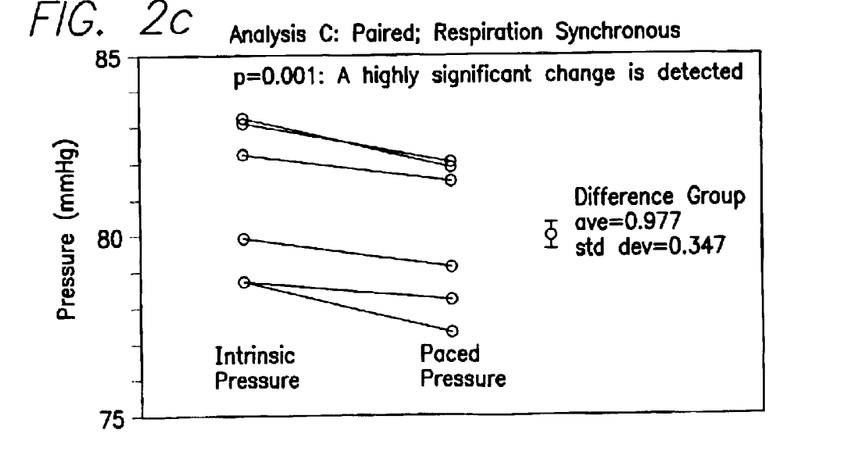
Figure 3:
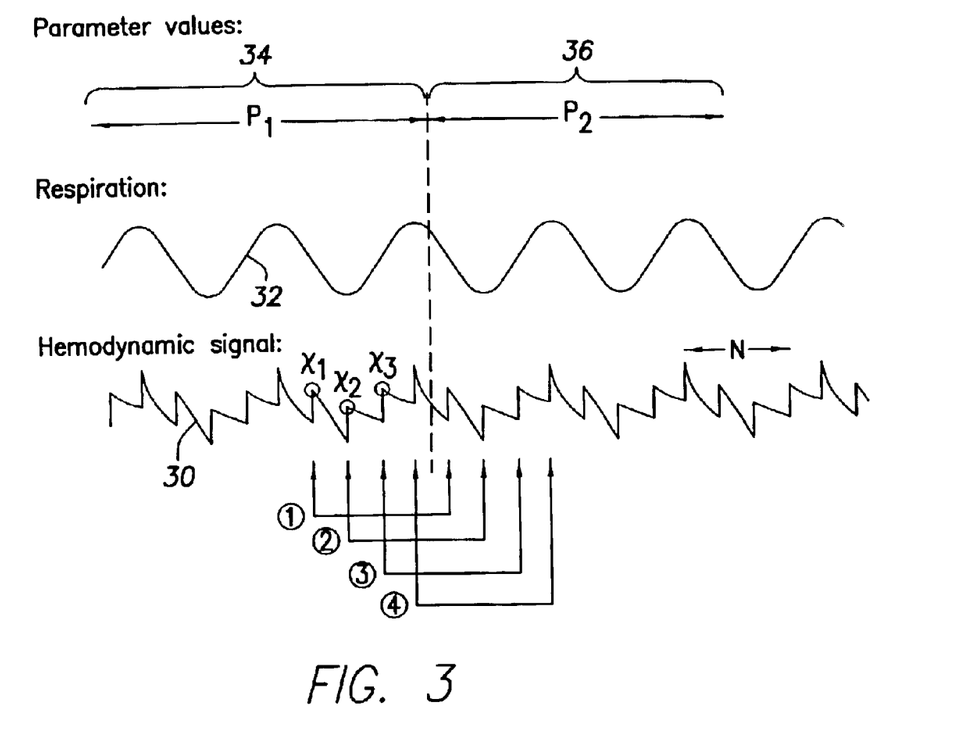
FIG. 3 is a graph of a hemodynamic signal versus respiration in accordance with one embodiment as disclosed herein.

Referring now to FIG. 3, hemodynamic signal 30 (e.g. heart beat) is contrasted chronologically to cyclical function 32 (in this example, respiration) over different periods of time $P_1$ 34 and $P_2$ 36. Periods $P_1$ 34 and $P_2$ 36 represent the two different environmental settings (e.g. paced and non-paced heart beats) over which the hemodynamic parameter is measured. Equation 1 below, and with reference to FIG. 3, summarizes the method employed in the example of FIGS. 1b (Analysis C) and 2c:

$$\delta = \sum_{i=1}^{M} x[i + nN] - \sum_{i=1}^{M} x[i] \qquad \text{Equation 1.}$$

where there are N beats per respiratory cycle and M beats (data points) to sum over, x(t) is the hemodynamic parameter of interest, and n−1 is the number of intervening respiratory cycles (i.e. when a comparison is made between adjacent respiratory cycles, n=1).

The results of the analysis methods of FIGS. 1a–1b and 2a–2c are summarized in Table 1 below. A p value of less than 0.05 is generally considered to be statistically significant, and the data is thus sufficient to conclude that arterial pressure is different for paced and non-paced heart beats. It is apparent that the method used with respect to FIG. 2c (Analysis C in FIG. 1b) is superior in its ability to detect significant changes in hemodynamic values despite the impact of cyclical body functions upon the particular hemodynamic parameter being monitored.

TABLE 1

| Pressure during Non-paced vs. Paced Heart Beats | | | |
|---|---|---|---|
| Analysis | Diastolic | Mean | Systolic |
| A - Unpaired | p = 0.50 | p = 0.24 | p = 0.43 |
| B - Paired, Asynchronous to Respiration | p = 0.88 | p = 0.46 | p = 0.72 |
| C - Paired, Synchronous to Respiration | p = 0.007 | p = 0.006 | p = 0.001 |

In accordance with another embodiment as disclosed herein, absolute measurements of a hemodynamic parameter may be taken by eliminating the effect of cyclical body functions, such as respiration (e.g., arterial pressure decreases when a patient breathes in). In this embodiment, once the cyclical function that affects the hemodynamic variable (i.e. the "noise" source that affects the true value of the hemodynamic variable) is identified, an absolute measure of the value of the hemodynamic variable of interest may be obtained by measuring and averaging the variable over an entire cycle, or multiple integral cycles, of the function so as to eliminate the noise caused by the function. With respect to the previous example, an absolute value of blood pressure could be obtained by measuring the pressure at every single heart beat during an integral number (1, 2, 3 . . . ) of breathing cycles (inhalation and exhalation) and averaging these values.

In accordance with yet another embodiment as disclosed herein, a hemodynamic variable may be tracked against multiple cyclical functions by measuring the hemodynamic variable at the same instant(s) within each cycle of each function and comparing the values obtained in subsequent cycles of each respective function. In this manner, it may be possible to detect significant changes in the hemodynamic variable even if the effects of any one of the functions upon the variable are so influential as to otherwise obscure such significant changes.

As previously mentioned, one application of the method of the invention is to program a pacemaker or other implantable cardiac stimulation device to analyze hemodynamic parameters as disclosed above and thus optimize device parameters such as the A-V delay by assessing the true impact of different parameter values on heart performance and adjusting the parameter accordingly. Thus, an implantable device may use a similar technique to optimize the pacing mode (e.g., atrial pacing, ventricular pacing, atrial and ventricular pacing). Further, an implantable cardiac defibrillator may use such a technique for arrhythmia discrimination by tracking significant absolute changes in the volume of blood pumped by the heart.

Although the illustrative example discussed above entails the measurement and comparison of discrete values, the methods disclosed are equally applicable to parameters that are measured continuously in time, such as time-averaged blood pressure. In such applications, the method may employed to perform analogous processing.

Figure 4:
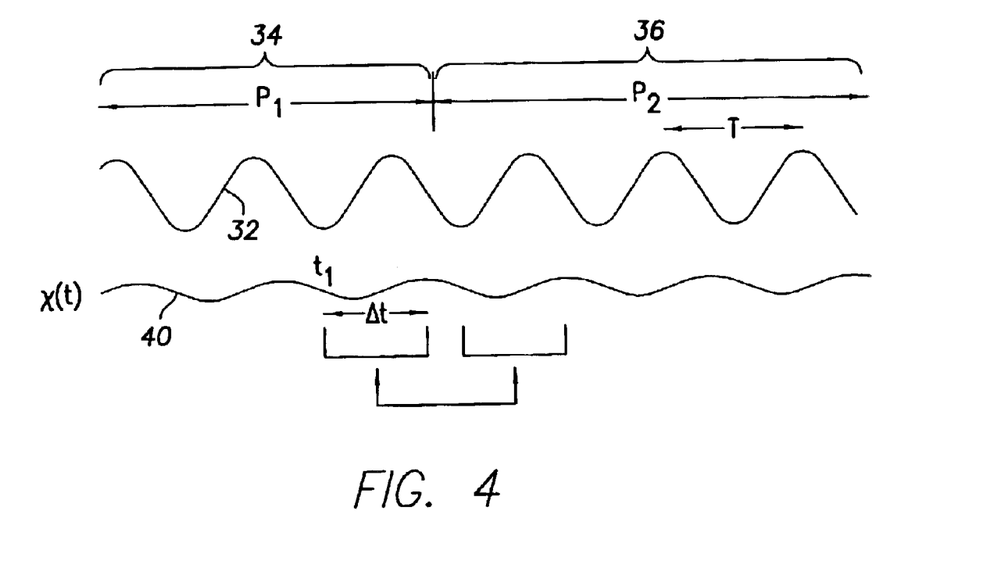
FIG. 4 is a graph of a hemodynamic signal versus respiration in accordance with another embodiment as disclosed herein.

Referring to FIG. 4, hemodynamic signal 40 (e.g. blood pressure) is shown to provide a continuous analog waveform x(t) over time periods $P_1$ 34 and $P_2$ 36, as previously discussed. Equation 2 below, with reference to FIG. 4, illustrates analogous processing according to the techniques disclosed herein:

$$\delta = \int_{t_1+nT}^{t_1+nT+\Delta t} x(t)\,dt - \int_{t_1}^{t_1+\Delta t} x(t)\,dt \qquad \text{Equation 2.}$$

where T is the length of time of a cycle of the relevant body function 32 (e.g. respiration), $\Delta t$ is the length of time over which to integrate the value of the hemodynamic parameter 40, and n−1 is the number of intervening cycles of the body function.

Figure 5:
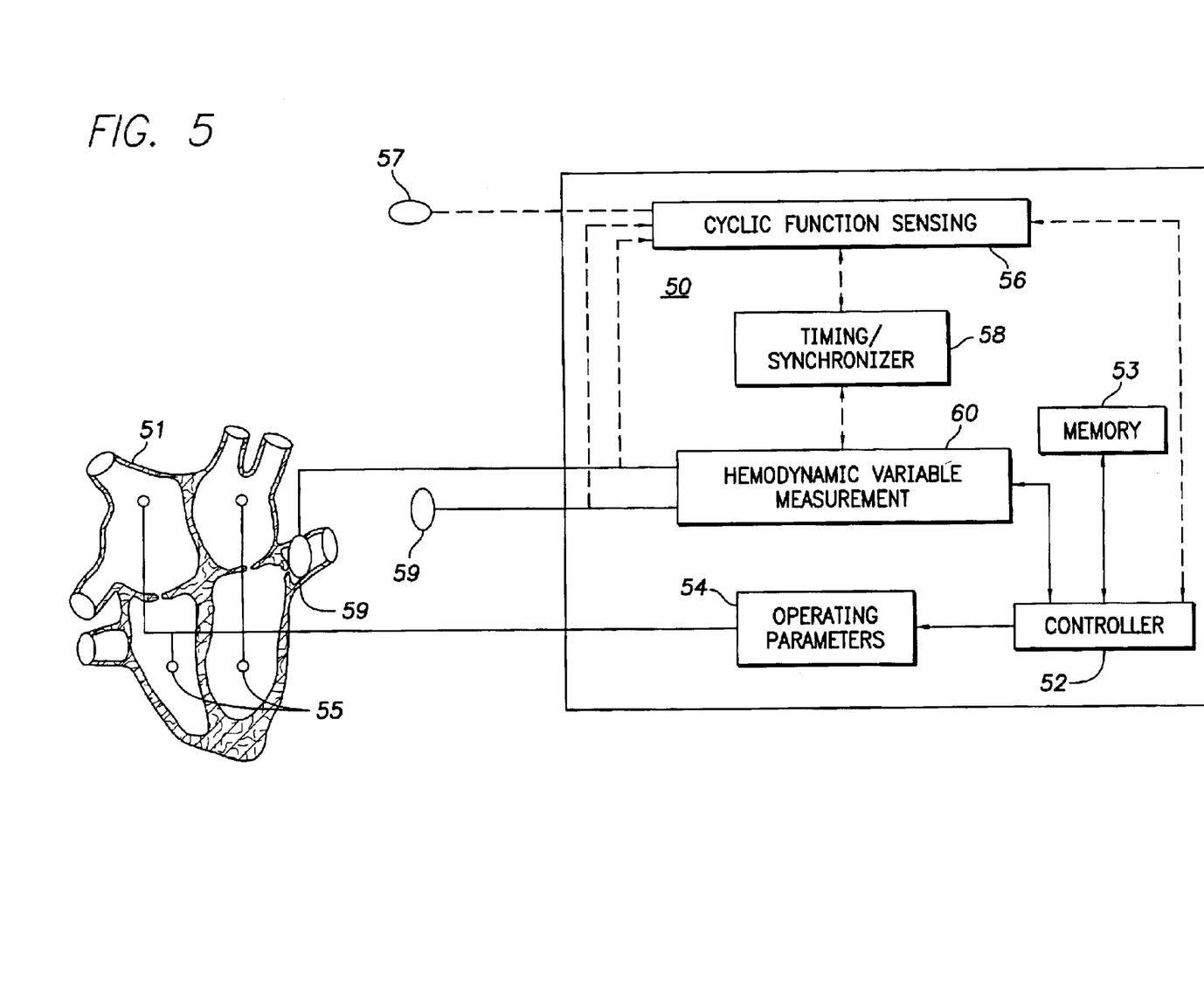
FIG. 5 is a functional block diagram of one embodiment of an implantable cardiac stimulation device for use with a technique as disclosed herein.

Referring now to FIG. 5, a functional diagram of cardiac stimulation device 50 implanted in a patient and functioning in accordance with a technique as disclosed herein includes controller 52. Controller 52 includes, or has access to, memory 53, and receives data and selects operating parameters 54 accordingly for cardiac leads 55 that are implanted in patient's heart 51 (e.g. the A-V delay). Cardiac device 50 further includes hemodynamic variable measurement hardware that drives and conditions the output of one or more hemodynamic sensors 59. A hemodynamic sensor 59 may sense the performance of patient's heart 51 and/or cardiovascular system. Examples of such sensors include, but are not limited to, sensors for photoplethysmography, pressure, cardiac output assessment by ultrasound or impedance plethysmography, cardiac acceleration, and heart sounds. Hemodynamic sensors 59 may be placed extravascularly, intravascularly, epicardially, and/or within the chambers of heart 51.

Hemodynamic sensors typically detect the cyclical fluctuation in the cardiac function that is induced by respiration. In addition to this respiration-induced modulation of the cardiovascular function, sensors may also direct sense respiration, such as through a motion artifact associated with breathing. In accordance with the invention, controller 52 may detect cyclical fluctuations in a hemodynamic signal associated with respiration or other causes, and characterize the frequency and phase of each such fluctuation. Controller 52 may detect such fluctuations in real time, i.e. simultaneously with the acquisition of the hemodynamic data, or may apply post-processing to the data after it has been acquired. In either embodiment, controller 52 compares hemodynamic data points that occur in corresponding phases of the respiratory cycle and then adjusts operating (e.g. pacing) parameters accordingly so as to optimize the performance of the patient's cardiovascular system.

Cardiac device 50 may include dedicated hardware such as timing/synchronizer 58 and cyclic function sensing circuitry 56 to perform or aid in performing cyclical function analysis. Cardiac device 50 may further include lung sensor 57 that is specifically designed to measure respiration, such as a thoracic impedance plethysmography sensor. In such an embodiment, timing/synchronizer circuitry 58 is connected to cyclic function sensing circuitry 56 as well as hemodynamic variable measurement circuitry 60, and received sensor data from both circuits. Timing/synchronizer circuitry 58 develops timing information from a source such as a hardware or a software timer, or from any other practicable source, and uses the timing information to track the cyclic function signal provided by hemodynamic sensor(s) 59 and/or lung sensor 57 and to further control hemodynamic variable measurement circuitry 60 to sample (i.e. measure) the hemodynamic variable signal provided by cardiac sensors 59 at the appropriate time or instant within any selected cycle of the cyclic function that is being tracked (e.g. respiration). The measured values of the hemodynamic variable are then provided by hemodynamic variable measurement circuitry 60 to controller 52 for processing and statistical analysis. Controller 52 may also be in communication with cyclic function sensing circuitry 56 to receive data from sensor 57 and/or to control the cyclic function sensing circuitry.

Figure 6:
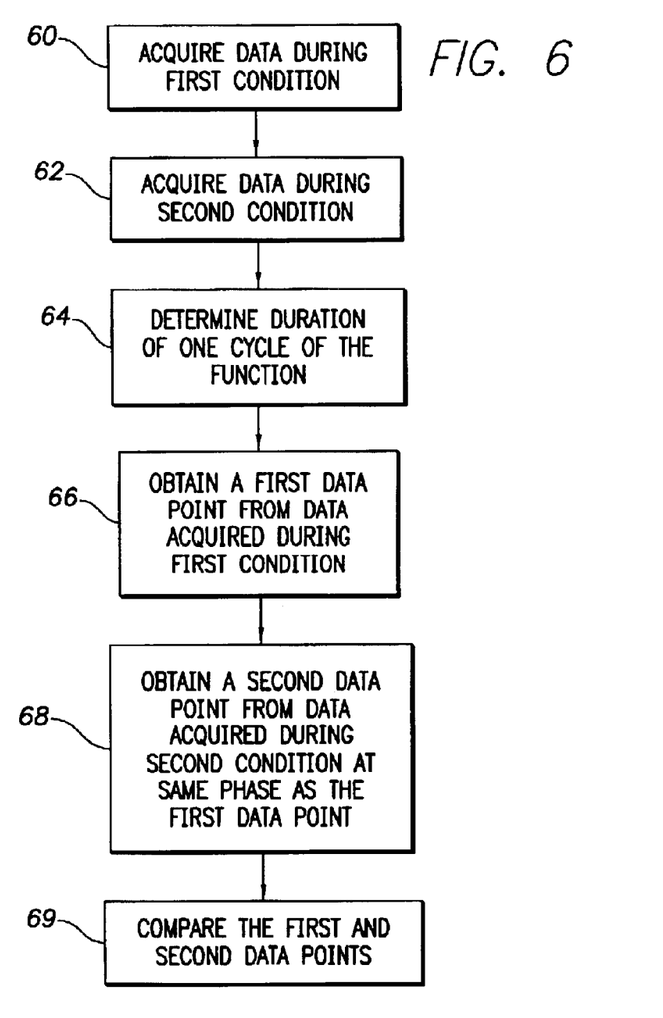
FIG. 6 is a flowchart illustrating steps performed in one embodiment of a technique as disclosed herein.

FIG. 6 is a flow chart depicting steps that may be taken in practicing a technique as disclosed herein. Data is acquired 60 during a first condition of the cyclical function of interest, and then acquired 62 during a second condition, such as acquiring heart beat data while pacing the heart with two different sets of pacing parameters, or during two different pacing modes. Data acquisition 60, 62 may be separate in time, but it is noted that it is convenient to acquire data continuously during a transition between two conditions. In the embodiment illustrated, post processing is utilized to determine 64 the period of the cyclical fluctuation of interest. This may be accomplished by analysis performed in the time domain or in the frequency domain, as is well known in the art of signal processing. A first data point is then selected 66 from the data acquired 60 during the first condition at a predetermined phase (or instant) of the cycle or at an arbitrarily selected phase. A second data point is subsequently selected 68 from the data acquired during the second condition 62 at the same phase as the first data point was selected 66. Finally, the first and second data points are compared 69 as previously described.

Figure 7:
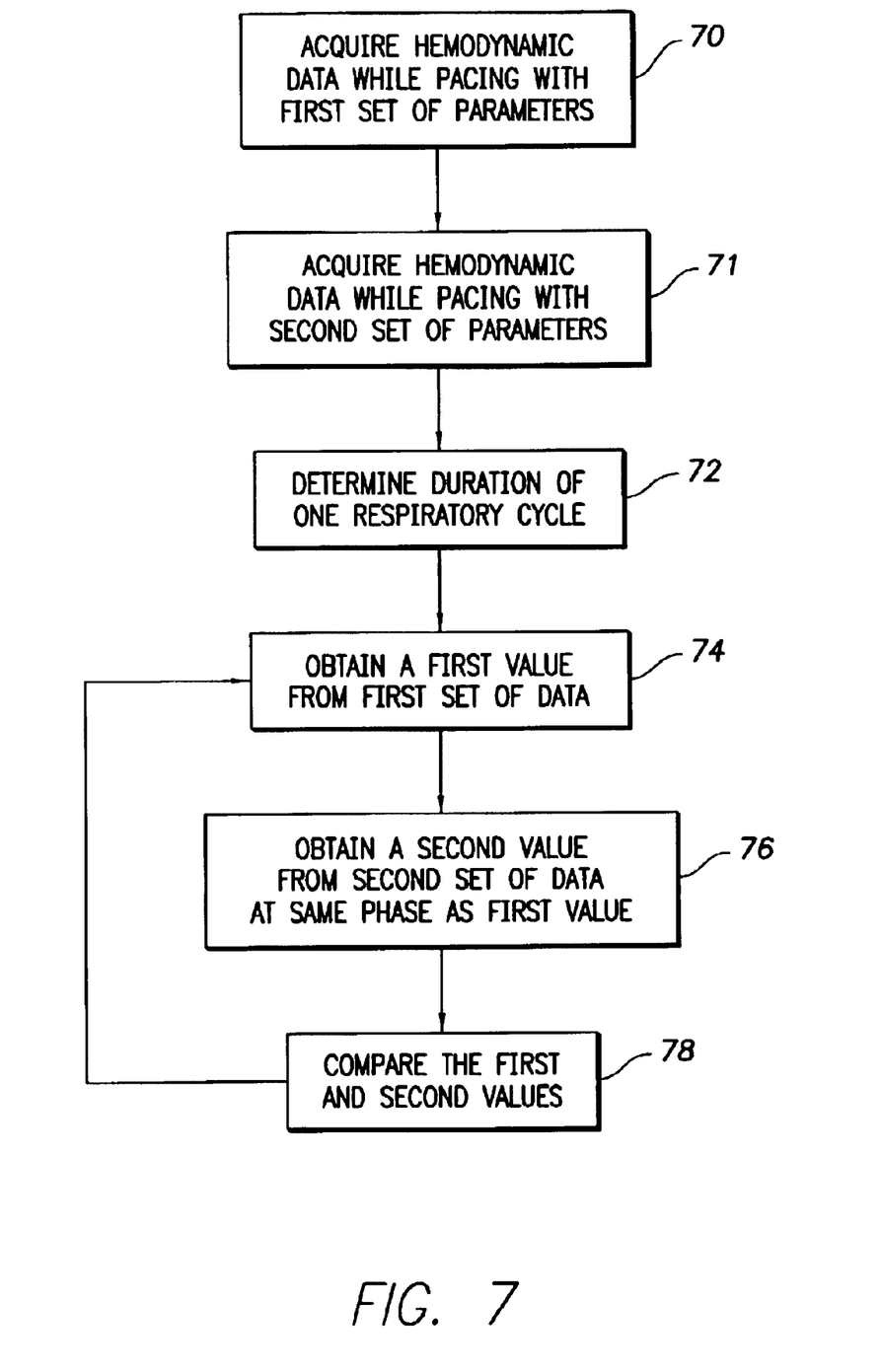
FIG. 7 is a flowchart illustrating steps performed in one embodiment of another technique as disclosed herein.

With reference to FIG. 7, an embodiment of a method according to the invention for optimizing pacing parameters in an implantable cardiac stimulation device is initiated by acquiring a first set of hemodynamic data 70 while the heart of the patient is paced in accordance with a first set of pacing parameters. A second set of hemodynamic data is then acquired 71 while the heart of the patient is paced in accordance with a second, different set of pacing parameters. For illustration purposes only, while optimizing pacing parameters, the first set of pacing parameters may include an A-V delay of 100 and an RV-LV delay of 50, while the second set of pacing parameters may include an A-V delay of 125 and an RV-LV delay of 75. As another illustrative example, the first set of pacing parameters may include VVI pacing and the second set may include DDD pacing.

After the two sets of hemodynamic data are acquired, the duration of the respiratory phase (i.e. one respiratory cycle) is determined 72 by time domain or frequency domain signal processing, as is known in the art. A first value of the hemodynamic function is next retrieved 74 from the first set of acquired data, and then a second value of the hemodynamic value is retrieved 76 at the same phase (instant) of the respiratory cycle from the second set of acquired data.

Synchronizing the phase at which the first and second values are retrieved is relatively straightforward because the duration of the respiratory cycle has been previously determined 72. Thus, for purposes of illustration only, if the respiratory cycle duration is determined to be 5 seconds, the first value may be taken at four seconds before the pacing parameters are changed, in which case the second value is taken at one second after the pacing parameters are changed. In this manner, the known lingering effects on the cardiovascular system from the previous pacing values can be minimized. For instance, because the contractility of the heart depends on preload, the effectiveness of pacing parameters can influence cardiac function for at least one heart beat after the new set of pacing parameters is used.

The two values are then compared 78. If averaging over a period of time is desired, the process is repeated with acquiring a first value 74. Averaging does not have to be performed over an entire cycle. Averaging over a portion of a cycle may be effective, and sometimes desirable, to avoid the transition effects described previously, provided that the values are sampled at the same phase of the function. The results of comparing the values 78 may be used to optimize the function of the cardiac device, such as its pacing intervals.

Figure 8:
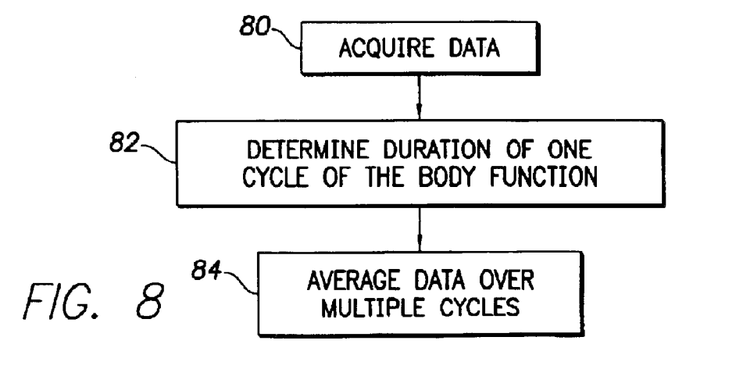
FIG. 8 is a flowchart illustrating steps performed in one embodiment of another technique as disclosed herein.

Referring now to FIG. 8, the method of the invention may be used to obtain an absolute measure of a hemodynamic variable that is not affected by other body functions. Thus, in one embodiment, the hemodynamic variable of interest is measured and data is acquired 80 over a predetermined period of time. The duration of one cycle of the body function of interest is then determined 82. Finally, the data acquired is averaged over multiple, whole cycles of the function to determine an absolute value for the hemodynamic variable of interest.

Figure 9:
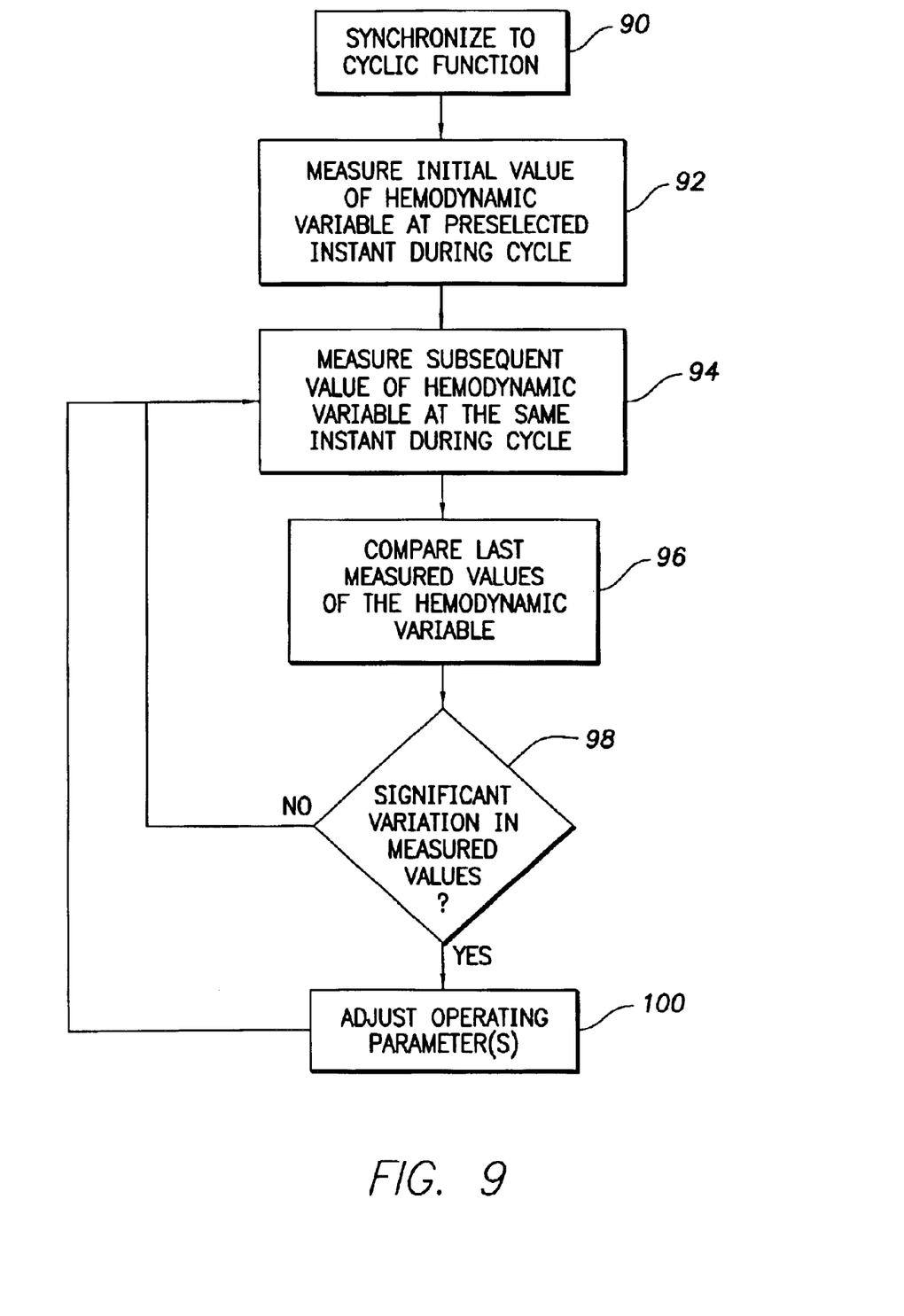
FIG. 9 is a flowchart illustrating steps performed in one embodiment of another technique as disclosed herein.

FIG. 9 is a flow chart depicting steps that may be taken in practicing another method as disclosed herein. In an embodiment of this method, the cyclical function of interest (e.g. respiration) is first identified and synchronized to 90, after which the hemodynamic variable of interest is initially measured 92 at a predetermined instant in a first cycle of the cyclical function. A subsequent measurement of the hemodynamic variable is then taken 94 at the same instant (i.e. phase) in a subsequent cycle of the cyclical function. The subsequent cycle may occur immediately following the previous cycle during which the initial measurement was taken, or alternatively may be spaced by any selected number cycles from the previous cycle. In the case of analogous processing, the hemodynamic variable may be time-averaged over a single cycle or alternatively over contiguous multiple cycles to obtain each single measured value.

The last two measured values are then compared 96 and the results analyzed 98 to assess whether the difference, if any, is statistically and/or physiologically significant. If the difference is not significant, the hemodynamic variable is again measured 94 and the process is repeated. If the difference is significant, the operating parameter(s) of the cardiac device are adjusted 100, then the hemodynamic variable is again measured 94, and the entire process is subsequently repeated.

Hemodynamic parameters may be measured by any practicable method, including but not limited to mechanical, optical, and ultrasound sensors. One such sensor, among others, is described in copending U.S. patent application Ser. No. 09/543,214 filed on Apr. 5, 2000, titled "Extravascular Hemodynamic Sensor," and incorporated herein in its entirety by reference thereto.

Having now described the invention in accordance with the requirements of the patent statutes, those skilled in this art will understand how to make changes and modifications to the present invention to meet their specific requirements or conditions. Such changes and modifications may be made without departing from the scope and spirit of the invention as disclosed herein.

What is claimed is:

1. A method of monitoring changes in a living body, the method comprising:

measuring a hemodynamic variable of the living body during two different cycles of a cyclical function of the body, the hemodynamic variable being measured at substantially the same instant in each cycle; and comparing values of the hemodynamic variable measured during the two different cycles;

wherein measuring the hemodynamic variable comprises measuring an average value of the hemodynamic variable for a length of time starting at substantially the same instant during each cycle.

2. The method of claim 1, wherein the hemodynamic variable is blood pressure.

3. The method of claim 1, wherein a cardiac device is selected from among the group of cardiac devices comprising pace makers, defibrillators, and cardioverters.

4. The method of claim 1, wherein the cyclical function is the heart beat.

5. The method of claim 1, wherein the cyclical function is selected from among the group of cyclical functions comprising circadian rhythm, digestion, and locomotion.

6. The method of claim 1, wherein the hemodynamic variable is blood flow rate.

7. A method of monitoring changes in a living body, the method comprising:

measuring a hemodynamic variable of the living body during two different cycles of a cyclical function of the body, the hemodynamic variable being measured at substantially the same instant in each cycle; and comparing values of the hemodynamic variable measured during the two different cycles;

wherein the cyclical function is respiration.

8. The method of claim 7, wherein the hemodynamic variable is selected from among the group of hemodynamic variables comprising volume of vasculature, volume of cardiac chambers, stroke volume, oxygen consumption, heart sounds, respiration rate, tidal volume, blood gases, pH, and acceleration of the myocardium.

9. The method of claim 7, further comprising:

stimulating a heart beat of the living body during one of the two different cycles of the cyclical function with a cardiac stimulation device.

10. The method of claim 9, wherein the cardiac stimulation device is implanted in the body.

11. The method of claim 9, further comprising:
adjusting any one or more of an atrio-ventricular delay, an interchamber delay, a RV-LV delay, and a LA-LV delay of the cardiac stimulation device in accordance with a difference between the measured values.

12. The method of claim 7, further comprising:
controlling a cardiac stimulation device in accordance with a difference between the measured values.

13. The method of claim 12, wherein the cardiac stimulation device is implanted in the body.

14. An apparatus for monitoring changes in a living body, comprising:
a detector configured to measure a hemodynamic variable of the living body during two different cycles of a cyclical function of the body and at substantially the same instant in each cycle; and
a controller configured to compare values of the hemodynamic variable measured during the two different cycles;
wherein the detector is configured for measuring an average value of the hemodynamic variable for a length of time starting at substantially the same instant during each cycle.

15. The apparatus of claim 14, wherein the detector is configured for measuring the hemodynamic variable during cycles of any one or more of the heart beat, respiration, circadian rhythm, digestion, and locomotion of the patient.

16. The apparatus of claim 14, wherein the detector is configured for measuring any one or more of the blood flow rate, blood pressure, volume of vasculature, volume of cardiac chambers, stroke volume, oxygen consumption, heart sounds, respiration rate, tidal volume, blood gases, pH, and acceleration of the myocardium of the living body.

17. The apparatus of claim 14, wherein the controller is configured for selecting an operating parameter of the apparatus in accordance with a difference between values of the hemodynamic variable measured during the two different cycles.

18. The apparatus of claim 14, wherein the apparatus is a cardiac stimulation device configured for stimulating the heart beat of the living body.

19. The apparatus of claim 18, wherein the controller is configured for selecting a pacing parameter of the apparatus in accordance with a difference between values of the hemodynamic variable measured during the two different cycles.

20. The apparatus of claim 19, wherein the pacing parameter is an atrio-ventricular delay, an interchamber delay, and RV-LV delay, or an LA-LV delay of the apparatus.

21. The apparatus of claim 18, wherein the apparatus is configured to be implanted in the body.

22. In an implantable cardiac stimulation device implanted in a patient's body, a method comprising:
measuring a hemodynamic variable of the body at a first instant during a first cycle of a selected cyclical function of the body;
operating the cardiac device to stimulate the heart of the body during a second cycle of the function;
measuring the hemodynamic variable at an instant during the second cycle that is substantially the same as the first instant; and
adjusting an operating parameter of the cardiac device in accordance with a difference between values of the hemodynamic variable measured during the first and second cycles;
wherein measuring the hemodynamic variable during each of the cycles comprises measuring the average value of the hemodynamic variable over substantially the same length of time during each cycle.

23. The method of claim 22, wherein the cyclical function is selected from among the group of functions comprising circadian rhythm, digestion, and locomotion.

24. The method of claim 22, wherein the hemodynamic variable is blood flow rate.

25. The method of claim 22, wherein the hemodynamic variable is blood pressure.

26. The method of claim 22, wherein the cyclical function is the heart beat.

27. A method of operating a cardiac stimulation device implanted in a patient and configured to provide pacing pulses to the heart of the patient, the method comprising:
measuring a hemodynamic variable of the patient at a first instant during a first respiratory cycle of the patient;
operating the cardiac device to stimulate the heart of the patient during a second respiratory cycle of the patient;
measuring the hemodynamic variable at an instant during the second respiratory cycle that is substantially the same as the first instant; and
adjusting any one or more of an atrio-ventricular delay, an interchamber delay, a RV-LV delay, and a LA-LV delay of the cardiac device in accordance with a difference between values of the hemodynamic variable measured during the first and second respiratory cycles.

28. The method of claim 27, wherein the hemodynamic variable is selected from among the group of hemodynamic variables comprising volume of vasculature, volume of cardiac chambers, stroke volume, oxygen consumption, heart sounds, respiration rate, tidal volume, blood gases, pH, and acceleration of the myocardium.

29. The method of claim 27, further comprising after adjusting one or more delays:
measuring the hemodynamic variable at a second instant during a third respiratory cycle of the patient;
operating the cardiac device to stimulate the heart of the patient during a fourth respiratory cycle of the patient;
measuring the hemodynamic variable at an instant during the fourth respiratory cycle that is substantially the same as the second instant; and
adjusting the one or more delays a second time in accordance with a difference between values of the hemodynamic variable measured during the third and fourth cycles.

30. The method of claim 29, wherein the first and second instants are substantially the same.

31. The method of claim 29, wherein adjusting the one or more delays comprises:
adjusting the one or more delays to maximize the value of the hemodynamic variable.

32. The method of claim 29, wherein adjusting the one or more delays comprises:
adjusting the one or more delays to minimize the value of the hemodynamic variable.

33. The method of claim 27, wherein the hemodynamic variable is blood flow rate.

34. The method of claim 27, wherein the hemodynamic variable is blood pressure.

35. In an implantable cardiac stimulation device implanted in patient's body, a method comprising:
measuring a hemodynamic variable of the body at a first instant during a first cycle of a selected cyclical function of the body;
operating the cardiac device to stimulate the heart of the body during a second cycle of the function;

measuring the hemodynamic variable at an instant during the second cycle that is substantially the same as the first instant; and adjusting an operating parameter of the cardiac device in accordance with a difference between values of the hemodynamic variable measured during the first and second cycles;

wherein the cyclical function is respiration.

36. The method of claim 35, wherein the hemodynamic variable is selected from among the group of hemodynamic variables comprising volume of vasculature, volume of cardiac chambers, stroke volume, oxygen consumption, heart sounds, respiration rate, tidal volume, blood gases, pH, and acceleration of the myocardium.

37. In an implantable cardiac stimulation device implanted in patient's body, a method comprising:

measuring a hemodynamic variable of the body at a first instant during a first cycle of a selected cyclical function of the body;

operating the cardiac device to stimulate the heart of the body during a second cycle of the function;

measuring the hemodynamic variable at an instant during the second cycle that is substantially the same as the first instant;

adjusting an operating parameter of the cardiac device in accordance with a difference between values of the hemodynamic variable measured during the first and second cycles; and after adjusting the operating parameter, measuring the hemodynamic variable at a second instant during a third cycle of the cyclical function, operating the cardiac device to stimulate the heart during a fourth cycle of the function, measuring the hemodynamic variable at an instant during the fourth cycle that is substantially the same as the second instant, and adjusting the operating parameter a second time in accordance with a difference between values of the hemodynamic variable measured during the third and fourth cycles;

wherein adjusting the parameter a second time further comprises adjusting the operating parameter in accordance with a difference between values of the hemodynamic variable measured during the second cycle and the fourth cycle.

38. The method of claim 37, wherein the first and second instants are substantially the same.

39. The method of claim 37, wherein the parameter is an atrio-ventricular delay, an interchamber delay, and RV-LV delay, or an LA-LV delay.

* * * * *